(12) United States Patent
Mitchell et al.

(10) Patent No.: US 9,179,678 B2
(45) Date of Patent: Nov. 10, 2015

(54) SUBSTITUTED [1,2,4]TRIAZOLES AND SUBSTITUTED TETRAZOLES AS HERBICIDES

(71) Applicant: SYNGENTA LIMITED, Bracknell (GB)

(72) Inventors: Glynn Mitchell, Bracknell (GB); Olivia Anabelle Sageot, Bracknell (GB)

(73) Assignee: Syngenta Limited, Guildford, Surrey (GB)

( * ) Notice: Subject to any disclaimer, the term of this patent is extended or adjusted under 35 U.S.C. 154(b) by 0 days.

(21) Appl. No.: 14/389,109

(22) PCT Filed: Mar. 27, 2013

(86) PCT No.: PCT/EP2013/056569
§ 371 (c)(1),
(2) Date: Sep. 29, 2014

(87) PCT Pub. No.: WO2013/144231
PCT Pub. Date: Oct. 3, 2013

(65) Prior Publication Data
US 2015/0087513 A1  Mar. 26, 2015

(30) Foreign Application Priority Data

Mar. 29, 2012 (GB) ................................... 1205654.5

(51) Int. Cl.
| | | |
|---|---|---|
| *A61K 31/41* | (2006.01) | |
| *A61K 31/4196* | (2006.01) | |
| *C07D 249/14* | (2006.01) | |
| *C07D 257/06* | (2006.01) | |
| *A01N 43/713* | (2006.01) | |
| *C07D 403/12* | (2006.01) | |
| *C07D 401/14* | (2006.01) | |
| *C07D 405/14* | (2006.01) | |
| *C07D 401/12* | (2006.01) | |
| *C07D 409/14* | (2006.01) | |
| *C07D 471/04* | (2006.01) | |
| *A01N 43/90* | (2006.01) | |

(52) U.S. Cl.
CPC .............. *A01N 43/713* (2013.01); *A01N 43/90* (2013.01); *C07D 401/12* (2013.01); *C07D 401/14* (2013.01); *C07D 403/12* (2013.01); *C07D 405/14* (2013.01); *C07D 409/14* (2013.01); *C07D 471/04* (2013.01)

(58) Field of Classification Search
CPC . A61K 31/41; A61K 31/4196; C07D 249/14; C07D 257/06
USPC ................ 514/381, 383; 548/251, 265.4
See application file for complete search history.

(56) References Cited

FOREIGN PATENT DOCUMENTS

| WO | 2010116122 | 10/2010 |
| WO | 2012028579 | 3/2012 |

OTHER PUBLICATIONS

International Search Report for International Application No. PCT/EP2013/056569; Completed on May 14, 2013.

*Primary Examiner* — Douglas M Willis
(74) *Attorney, Agent, or Firm* — James Cueva

(57) ABSTRACT

The present invention relates to compounds of Formula (I), or an agronomically acceptable salt of said compounds wherein $A^1, A^2, A^3, A^4, A^5, X, R^1, R^2$ and $R^6$ are as defined herein. The invention further relates to herbicidal compositions which comprise a compound of Formula (I), and to their use for controlling weeds, in particular in crops of useful plants.

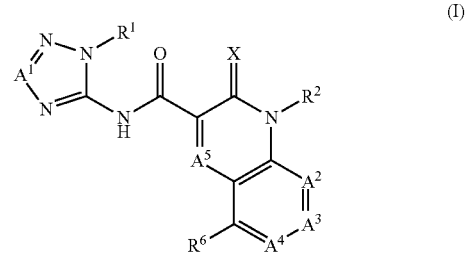

(I)

14 Claims, No Drawings

SUBSTITUTED [1,2,4]TRIAZOLES AND SUBSTITUTED TETRAZOLES AS HERBICIDES

This application is a 371 of International Application No. PCT/EP2013/056569 filed Mar. 27, 2013, which claims priority to GB 1205654.5, filed Mar. 29, 2012, the contents of which are incorporated herein by reference.

The present invention relates to novel herbicidal compounds, to processes for their preparation, to herbicidal compositions which comprise the novel derivatives, and to their use for controlling weeds, in particular in crops of useful plants, or for inhibiting plant growth.

Herbicidal N-(Tetrazol-5-yl) and N-(Triazol-5-yl) arylcarboxamides are known from WO2012/028579. Herbicidal oxopyrazine derivatives are known from, for example, WO2009/016841. Herbicidal oxopyridine compounds are known from, for example, WO2010/089993, WO2010/116122 and WO2012/045721. The present invention relates to the provision of further such compounds. Thus, according to the present invention there is provided a compound of Formula (I):

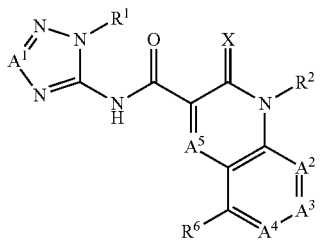

(I)

or an agronomically acceptable salt thereof, wherein: —

X is O or S;
$A^1$ is CH or N;
$A^2$ is N or $CR^3$;
$A^3$ is N or $CR^4$;
$A^4$ is N or $CR^5$;
$A^5$ is N or CH;
wherein $R^1$ is selected from the group consisting of $C_1$-$C_6$ alkyl, $C_1$-$C_6$ haloalkyl and $C_1$-$C_6$alkoxy-$C_1$-$C_3$alkyl;

$R^2$ is selected from the group consisting of hydrogen, $C_1$-$C_6$alkyl, $C_1$-$C_6$haloalkyl, $C_1$-$C_3$alkoxy-$C_1$-$C_3$alkyl, $C_1$-$C_3$haloalkoxy-$C_1$-$C_3$alkyl, $C_1$-$C_3$ alkoxy-$C_1$-$C_3$alkoxy-$C_1$-$C_3$-alkyl, $C_1$-$C_3$alkoxy-$C_1$-$C_3$-haloalkyl, $C_1$-$C_3$-alkoxy-$C_1$-$C_3$-alkoxy-$C_1$-$C_3$-haloalkyl, $C_4$-$C_6$-oxasubstituted cycloalkoxy-$C_1$-$C_3$-alkyl, $C_4$-$C_6$-oxasubstitutedcycloalkyl-$C_1$-$C_3$-alkoxy-$C_1$-$C_3$-alkyl, $C_4$-$C_6$-oxasubstitutedcycloalkoxy-$C_1$-$C_3$-haloalkyl, $C_4$-$C_6$-oxasubstitutedcycloalkyl-$C_1$-$C_3$-alkoxy-$C_1$-$C_3$-haloalkyl, ($C_1$-$C_3$ alkanesulfonyl-$C_1$-$C_3$ alkylamino)-$C_1$-$C_3$ alkyl, ($C_1$-$C_3$ alkanesulfonyl-$C_3$-$C_4$ cycloalkylamino)-$C_1$-$C_3$alkyl, $C_1$-$C_6$alkylcarbonyl-$C_1$-$C_3$alkyl, $C_3$-$C_6$cycloalkyl-$C_2$-$C_6$alkenyl, $C_2$-$C_6$alkynyl, $C_2$-$C_6$-alkenyl, $C_2$-$C_6$-haloalkenyl, cyano-$C_1$-$C_6$-alkyl, arylcarbonyl-$C_1$-$C_3$-alkyl (wherein the aryl may be optionally substituted with one or more substituents from the group consisting of halogen, $C_1$-$C_3$-alkoxy, $C_1$-$C_3$-alkyl, $C_1$-$C_3$ haloalkyl), aryl-$C_1$-$C_6$alkyl, aryloxy-$C_1$-$C_6$alkyl (wherein both cases the aryl may be optionally substituted with one or more substituents from the group consisting of halogen, $C_1$-$C_3$-alkoxy, $C_1$-$C_3$-alkyl, $C_1$-$C_3$ haloalkyl), and a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more substituents selected from the group consisting of $C_1$-$C_3$alkyl, $C_1$-$C_3$haloalkyl, $C_2$-$C_3$alkenyl, $C_2$-$C_3$alkynyl, $C_1$-$C_3$ alkoxy, $C_1$-$C_3$ haloalkoxy, $C_1$-$C_6$alkyl-S(O)p-, $C_1$-$C_6$haloalkyl-S(O)p-, aryl, aryl-S(O)p, heteroaryl-S(O)p, aryloxy, heteroaryloxy, $C_1$-$C_3$ alkoxycarbonyl, $C_1$-$C_3$ alkylamino-S(O)p-, $C_1$-$C_3$ alkylamino-S(O)p-$C_1$-$C_3$ alkyl, $C_1$-$C_3$ dialkylamino-S(O)p-, $C_1$-$C_3$ dialkylamino-S(O)p-$C_1$-$C_3$ alkyl, $C_1$-$C_3$ alkylaminocarbonyl-, $C_1$-$C_3$ alkylaminocarbonyl-$C_1$-$C_3$ alkyl, $C_1$-$C_3$ dialkylaminocarbonyl, $C_1$-$C_3$ dialkylaminocarbonyl-$C_1$-$C_3$ alkyl, $C_1$-$C_3$ alkylcarbonylamino, $C_1$-$C_3$ alkyl-S(O)p-amino, halogen, cyano and nitro; the heteroaryl substituents containing one to three heteroatoms each independently selected from the group consisting of oxygen, nitrogen and sulphur, and wherein the aryl or heteroaryl component may be optionally substituted by one or more substituents selected from the group consisting of halogen, $C_1$-$C_3$alkyl, $C_1$-$C_3$haloalkyl, $C_1$-$C_3$ alkoxy, $C_1$-$C_3$ haloalkoxy, phenyl, cyano and nitro;

$R^3$ is selected from the group consisting of hydrogen, halogen, $C_1$-$C_6$alkyl, $C_1$-$C_6$haloalkyl, $C_1$-$C_6$alkylcarbonyl-$C_1$-$C_3$alkyl, $C_3$-$C_6$cycloalkyl-$C_2$-$C_6$alkenyl for example cyclohexylmethylenyl, $C_3$-$C_6$alkynyl (for example propargyl), $C_2$-$C_6$-alkenyl (for example allyl), $C_1$-$C_6$alkoxy $C_1$-$C_6$alkyl, cyano-$C_1$-$C_6$-alkyl, arylcarbonyl-$C_1$-$C_3$-alkyl (wherein the aryl may be optionally substituted with one or more substituents selected from the group consisting of halo, $C_1$-$C_3$-alkoxy, $C_1$-$C_3$-alkyl, $C_1$-$C_3$ haloalkyl), aryl-$C_1$-$C_6$alkyl (wherein the aryl may be optionally substituted with one or more substituents from the group consisting of halo, $C_1$-$C_3$-alkoxy, $C_1$-$C_3$-alkyl, $C_1$-$C_3$ haloalkyl), $C_1$-$C_6$alkoxy$C_1$-$C_6$alkoxy $C_1$-$C_6$alkyl, aryl, a 5 or 6-membered heteroaryl, a 5 or 6-membered heteroaryl-$C_1$-$C_3$-alkyl and heterocyclyl-$C_1$-$C_3$-alkyl, the heteroaryl or heterocyclyl containing one to three heteroatoms each independently selected from the group consisting of oxygen, nitrogen and sulphur, and wherein the aryl, heterocyclyl or heteroaryl component may be optionally substituted by one or more substituents from the group consisting of halogen, $C_1$-$C_3$alkyl, $C_1$-$C_3$haloalkyl and $C_1$-$C_3$ alkoxy, cyano and nitro;

$R^4$ is selected from the group consisting of hydrogen, cyano, nitro, halogen, hydroxyl, sulfhydryl, $C_1$-$C_6$alkyl, $C_3$-$C_6$cycloalkyl, $C_1$-$C_6$haloalkyl, $C_2$-$C_6$haloalkenyl, $C_2$-$C_6$alkenyl, aryl-$C_2$-$C_6$alkenyl, $C_2$-$C_6$alkynyl, $C_1$-$C_6$alkoxy, $C_4$-$C_7$ cycloalkoxy, $C_1$-$C_6$haloalkoxy, $C_1$-$C_6$alkyl-S(O)p, $C_3$-$C_6$cycloalkyl-S(O)p $C_1$-$C_6$haloalkyl-S(O)p, $C_3$-$C_6$ halocycloalkyl-S(O)p, $C_1$-$C_6$alkylcarbonylamino, ($C_1$-$C_6$alkylcarbonyl)$C_1$-$C_3$alkylamino, ($C_3$-$C_6$cycloalkylcarbonyl)amino, ($C_3$-$C_6$cycloalkylcarbonyl)$C_1$-$C_3$alkylamino, arylcarbonylamino, (arylcarbonyl)-$C_{1-3}$alkylamino, (heteroarylcarbonyl)amino, (heteroarylcarbonyl)$C_1$-$C_3$alkylamino, amino, $C_1$-$C_6$alkylamino, $C_2$-$C_6$dialkylamino, $C_2$-$C_6$alkenylamino, $C_1$-$C_6$alkoxy-$C_2$-$C_6$-alkylamino, ($C_1$-$C_6$alkoxy-$C_2$-$C_4$-alkyl)-$C_1$-$C_6$-alkylamino, $C_3$-$C_6$ cycloalkylamino, $C_3$-$C_6$ cycloalloalkylamino, $C_1$-$C_3$alkoxy-$C_3$-$C_6$ cycloalkylamino, $C_3$-$C_6$ alkynylamino, dialkylamino in which the substituents join to form a 4-6 membered ring (e.g pyrrolidinyl, piperidinyl) optionally containing oxygen (e.g morpholinyl) and/or optionally substituted by $C_1$-$C_3$-alkoxy and/or halogen (especially fluorine), $C_2$-$C_6$dialkylaminosulfonyl, $C_1$-$C_6$alkylaminosulfonyl, $C_1$-$C_6$alkoxy-$C_1$-$C_6$alkyl, $C_1$-$C_6$alkoxy-$C_2$-$C_6$alkoxy, $C_1$-$C_6$alkoxy-$C_2$-$C_6$ alkoxy-$C_1$-$C_6$-alkyl, $C_3$-$C_6$alkenyl-$C_2$-$C_6$alkoxy, $C_3$-$C_6$alkynyl-$C_1$-$C_6$alkoxy, $C_1$-$C_6$alkoxycarbonyl, $C_1$-$C_6$alkylcarbonyl, $C_1$-$C_4$alkylenyl-S(O)p-$R^7$, $C_1$-$C_4$alkylenyl-$CO_2$—$R^7$, $C_1$-$C_4$alkylenyl-(CO)N—$R^7R^7$, aryl (e.g. phenyl), aryl $C_1$-$C_3$alkyl, aryl-S(O)p, heteroaryl-S(O)p, aryloxy (e.g phenoxy), a 5 or 6-membered heteroaryl, heteroaryl $C_1$-$C_3$ alkyl and heteroaryloxy, the heteroaryl containing one to three heteroatoms, each independently selected from the group consisting of oxygen, nitrogen and sulphur, wherein the aryl or heteroaryl component may be optionally substituted by one or more substituents selected from the group consisting of $C_1$-$C_3$alkyl, $C_1$-$C_3$haloalkyl, $C_1$-$C_3$ alkoxy, $C_1$-$C_3$haloalkoxy, halo, cyano and nitro;

$R^5$ is selected from the group consisting of hydrogen, fluorine, chlorine, hydroxyl, $C_1$-$C_3$ haloalkyl and methyl;

$R^6$ is selected from the group consisting of hydrogen, chloro, fluoro and methyl;

$R^7$ is independently selected from the group consisting of hydrogen and $C_1$-$C_6$alkyl; and p=0, 1 or 2.

Halogen (or halo) encompasses fluorine, chlorine, bromine or iodine. The same correspondingly applies to halogen in the context of other definitions, such as haloalkyl or halophenyl.

Haloalkyl groups having a chain length of from 1 to 6 carbon atoms are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl, heptafluoro-n-propyl and perfluoro-n-hexyl.

Alkoxy groups preferably have a chain length of from 1 to 6 carbon atoms. Alkoxy is, for example, methoxy, ethoxy, propoxy, isopropoxy, n-butoxy, isobutoxy, sec-butoxy or tert-butoxy or a pentyloxy or hexyloxy isomer, preferably methoxy and ethoxy. It should also be appreciated that two alkoxy substituents present on the same carbon atom.

Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy or 2,2,2-trichloroethoxy, preferably difluoromethoxy, 2-chloroethoxy or trifluoromethoxy.

$C_1$-$C_6$alkyl-S— (alkylthio) is, for example, methylthio, ethylthio, propylthio, isopropylthio, n-butylthio, isobutylthio, sec-butylthio or tert-butylthio, preferably methylthio or ethylthio.

$C_1$-$C_6$alkyl-S(O)— (alkylsulfinyl) is, for example, methylsulfinyl, ethylsulfinyl, propylsulfinyl, isopropylsulfinyl, n-butylsulfinyl, isobutylsulfinyl, sec-butylsulfinyl or tert-butylsulfinyl, preferably methylsulfinyl or ethylsulfinyl.

$C_1$-$C_6$alkyl-$S(O)_2$— (alkylsulfonyl) is, for example, methylsulfonyl, ethylsulfonyl, propylsulfonyl, isopropylsulfonyl, n-butylsulfonyl, isobutylsulfonyl, sec-butylsulfonyl or tert-butylsulfonyl, preferably methylsulfonyl or ethylsulfonyl.

Alkylamino is, for example, methylamino, ethylamino, n-propylamino, isopropylamino or a butylamino isomer. Dialkylamino is, for example, dimethylamino, methylethylamino, diethylamino, n-propylmethylamino, dibutylamino or diisopropylamino. Preference is given to alkylamino groups having a chain length of from 1 to 4 carbon atoms.

Alkoxyalkyl groups preferably have from 1 to 6 carbon atoms. Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

In a preferred embodiment of the invention X is O.

In another embodiment of the present invention is a compound of Formula (I) wherein $A^1$ is N.

In another preferred embodiment of the present invention, the compound of Formula (I) is selected from the group consisting of (i) wherein $A^2$ is $CR^3$, $A^3$ is $CR^4$, $A^4$ is $CR^5$ and $A^5$ is CH, (ii) wherein $A^2$ is $CR^3$, $A^3$ is N, $A^4$ is $CR^5$ and $A^5$ is CH, (iii) wherein $A^2$ is N, $A^3$ is $CR^4$, $A^4$ is $CR^5$ and $A^5$ is CH, (iv) wherein $A^2$ is $CR^3$, $A^3$ is $CR^4$, $A^4$ is N and $A^5$ is CH, $A^2$ is $CR^3$, (v) wherein $A^2$ is $CR^3$, $A^3$ is $CR^4$, $A^4$ is $CR^5$ and $A^5$ is N and (vi) wherein $A^2$ is N, $A^3$ is $CR^4$, $A^4$ is $CR^5$ and $A^5$ is N. Especially preferred is wherein (i) $A^2$ is $CR^3$, $A^3$ is $CR^4$, $A^4$ is $CR^5$ and $A^5$ is N or (ii) wherein $A^2$ is N, $A^3$ is $CR^4$, $A^4$ is $CR^5$ and $A^5$ is CH.

In another embodiment of the present invention is a compound of Formula (I) wherein $R^1$ is methyl or ethyl.

In another embodiment, $R^2$ is selected from the group consisting of $C_1$-$C_6$alkyl, aryl (especially phenyl) and a 5 or 6-membered heteroaryl containing one to three heteroatoms each independently selected from the group consisting of oxygen, nitrogen and sulphur, and wherein the aryl or heteroaryl may be optionally substituted by one or more substituents selected from the group consisting of halogen, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)p-, $C_1$-$C_6$haloalkyl-S(O)p-, cyano and nitro. In a more preferred embodiment, $R^2$ is a $C_1$-$C_6$alkyl or optionally substituted aryl selected from the group consisting of phenyl, phenoxy, phenoxy-$C_1$-$C_6$alkyl, benzyl, thiophenyl, 1,4 benzodioxinyl, 1,3 benzodioxoleyl, furanyl, naphthyl and pyridyl.

Especially preferred is wherein $R^2$ is an optionally substituted aryl selected from the group consisting of phenyl, thiophenyl and pyridyl, most preferably wherein $R^2$ is phenyl optionally substituted by one or more substituents selected from the group consisting of halogen, $C_1$-$C_3$alkyl (preferably methyl or ethyl), $C_1$-$C_3$haloalkyl (preferably trifluoromethyl-), $C_2$-$C_3$alkenyl (preferably vinyl), $C_1$-$C_3$ alkoxy (preferably methoxy- or ethoxy-), $C_1$-$C_3$ haloalkoxy (preferably trifluromethoxy-), methylthio-, cyano and nitro.

In another embodiment, $R^3$ is selected from the group consisting of hydrogen, halogen and $C_1$-$C_6$alkyl, most preferably hydrogen.

In another embodiment $R^4$ is selected from the group consisting of hydrogen, halogen, $C_1$-$C_6$alkyl (preferably methyl) and $C_1$-$C_6$haloalkyl (preferably trifluoromethyl-). Hydrogen or chlorine are particularly preferred.

In another embodiment $R^5$ is hydrogen or halogen (preferably fluorine or chlorine).

In another embodiment, $R^6$ is selected from the group consisting of hydrogen, halogen (especially chlorine) and methyl. Hydrogen is particularly preferred.

Compounds of Formula I may contain asymmetric centres and may be present as a single enantiomer, pairs of enantiomers in any proportion or, where more than one asymmetric centre are present, contain diastereoisomers in all possible ratios. Typically one of the enantiomers has enhanced biological activity compared to the other possibilities.

Similarly, where there are disubstituted alkenes, these may be present in E or Z form or as mixtures of both in any proportion.

Furthermore, compounds of Formula I may be in equilibrium with alternative tautomeric forms. It should be appreciated that all tautomeric forms (single tautomer or mixtures thereof), racemic mixtures and single isomers are included within the scope of the present invention.

The present invention also includes agronomically acceptable salts that the compounds of Formula I may form with amines (for example ammonia, dimethylamine and triethylamine), alkali metal and alkaline earth metal bases or quaternary ammonium bases. Among the alkali metal and alkaline earth metal hydroxides, oxides, alkoxides and hydrogen carbonates and carbonates used as salt formers, emphasis is to be given to the hydroxides, alkoxides, oxides and carbonates of lithium, sodium, potassium, magnesium and calcium, but especially those of sodium, magnesium and calcium. The corresponding trimethylsulfonium salt may also be used.

The compounds of Formula (I) according to the invention can be used as herbicides by themselves, but they are generally formulated into herbicidal compositions using formulation adjuvants, such as carriers, solvents and surface-active agents (SFAs). Thus, the present invention further provides a herbicidal composition comprising a herbicidal compound according to any one of the previous claims and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The herbicidal compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The composition of the present may further comprise at least one additional pesticide. For example, the compounds according to the invention can also be used in combination with other herbicides or plant growth regulators. In a preferred embodiment the additional pesticide is a herbicide and/or herbicide safener. Examples of such mixtures are (in which 'I' represents a compound of Formula I). I+acetochlor, I+acifluorfen, I+acifluorfen-sodium, I+aclonifen, I+acrolein, I+alachlor, I+alloxydim, I+ametryn, I+amicarbazone, I+amidosulfuron, I+aminopyralid, I+amitrole, I+anilofos, I+asulam, I+atrazine, I+azafenidin, I+azimsulfuron, I+BCPC, I+beflubutamid, I+benazolin, I+bencarbazone, I+benfluralin, I+benfuresate, I+bensulfuron, I+bensulfuron-methyl, I+bensulide, I+bentazone, I+benzfendizone, I+benzobicyclon, I+benzofenap, I+bicyclopyrone, I+bifenox, I+bilanafos, I+bispyribac, I+bispyribac-sodium, I+borax, I+bromacil, I+bromobutide, I+bromoxynil, I+butachlor, I+butamifos, I+butralin, I+butroxydim, I+butylate, I+cacodylic acid, I+calcium chlorate, I+cafenstrole, I+carbetamide, I+carfentrazone, I+carfentrazone-ethyl, I+chlorflurenol, I+chlorflurenol-methyl, I+chloridazon, I+chlorimuron, I+chlorimuron-ethyl, I+chloroacetic acid, I+chlorotoluron, I+chlorpropham, I+chlorsulfuron, I+chlorthal, I+chlorthal-dimethyl, I+cinidon-ethyl, I+cinmethylin, I+cinosulfuron, I+cisanilide, I+clethodim, I+clodinafop, I+clodinafop-propargyl, I+clomazone, I+clomeprop, I+clopyralid, I+cloransulam, I+cloransulam-methyl, I+cyanazine, I+cycloate, I+cyclosulfamuron, I+cycloxydim, I+cyhalofop, I+cyhalofop-butyl, I+2,4-D, I+daimuron, I+dalapon, I+dazomet, I+2,4-DB, I+I+desmedipham, I+dicamba, I+dichlobenil, I+dichlorprop, I+dichlorprop-P, I+diclofop, I+diclofop-methyl, I+diclosulam, I+difenzoquat, I+difenzoquat metilsulfate, I+diflufenican, I+diflufenzopyr, I+dimefuron, I+dimepiperate, I+dimethachlor, I+dimethametryn, I+dimethenamid, I+dimethenamid-P, I+dimethipin, I+dimethylarsinic acid, I+dinitramine, I+dinoterb, I+diphenamid, I+dipropetryn, I+diquat, I+diquat dibromide, I+dithiopyr, I+diuron, I+endothal, I+EPTC, I+esprocarb, I+ethalfluralin, I+ethametsulfuron, I+ethametsulfuron-methyl, I+ethephon, I+ethofumesate, I+ethoxyfen, I+ethoxysulfuron, I+etobenzanid, I+fenoxaprop-P, I+fenoxaprop-P-ethyl, I+fentrazamide, I+ferrous sulfate, I+flamprop-M, I+flazasulfuron, I+florasulam, I+fluazifop, I+fluazifop-butyl, I+fluazifop-P, I+fluazifop-P-butyl, I+fluazolate, I+flucarbazone, I+flucarbazone-sodium, I+flucetosulfuron, I+fluchloralin, I+flufenacet, I+flufenpyr, I+flufenpyr-ethyl, I+flumetralin, I+flumetsulam, I+flumiclorac, I+flumiclorac-pentyl, I+flumioxazin, I+flumipropin, I+fluometuron, I+fluoroglycofen, I+fluoroglycofen-ethyl, I+fluoxaprop, I+flupoxam, I+flupropacil, I+flupropanate, I+flupyrsulfuron, I+flupyrsulfuron-methyl-sodium, I+flurenol, I+fluridone, I+flurochloridone, I+fluroxypyr, I+flurtamone, I+fluthiacet, I+fluthiacet-methyl, I+fomesafen, I+foramsulfuron, I+fosamine, I+glufosinate, I+glufosinate-ammonium, I+glyphosate, I+halauxifen, I+halosulfuron, I+halosulfuron-methyl, I+haloxyfop, I+haloxyfop-P, I+hexazinone, I+imazamethabenz, I+imazamethabenz-methyl, I+imazamox, I+imazapic, I+imazapyr, I+imazaquin, I+imazethapyr, I+imazosulfuron, I+indanofan, I+indaziflam, I+iodomethane, I+iodosulfuron, I+iodosulfuron-methyl-sodium, I+ioxynil, I+isoproturon, I+isouron, I+isoxaben, I+isoxachlortole, I+isoxaflutole, I+isoxapyrifop, I+karbutilate, I+lactofen, I+lenacil, I+linuron, I+mecoprop, I+mecoprop-P, I+mefenacet, I+mefluidide, I+mesosulfuron, I+mesosulfuron-methyl, I+mesotrione, I+metam, I+metamifop, I+metamitron, I+metazachlor, I+methabenzthiazuron, I+methazole, I+methylarsonic acid, I+methyldymron, I+methyl isothiocyanate, I+metolachlor, I+S-metolachlor, I+metosulam, I+metoxuron, I+metribuzin, I+metsulfuron, I+metsulfuron-methyl, I+molinate, I+monolinuron, I+naproanilide, I+napropamide, I+naptalam, I+neburon, I+nicosulfuron, I+n-methyl glyphosate, I+nonanoic acid, I+norflurazon, I+oleic acid (fatty acids), I+orbencarb, I+orthosulfamuron, I+oryzalin, I+oxadiargyl, I+oxadiazon, I+oxasulfuron, I+oxaziclomefone, I+oxyfluorfen, I+paraquat, I+paraquat dichloride, I+pebulate, I+pendimethalin, I+penoxsulam, I+pentachlorophenol, I+pentanochlor, I+pentoxazone, I+pethoxamid, I+phenmedipham, I+picloram, I+picolinafen, I+pinoxaden, I+piperophos, I+pretilachlor, I+primisulfuron, I+primisulfuron-methyl, I+prodiamine, I+profoxydim, I+prohexadione-calcium, I+prometon, I+prometryn, I+propachlor, I+propanil, I+propaquizafop, I+propazine, I+propham, I+propisochlor, I+propoxycarbazone, I+propoxycarbazone-sodium, I+propyzamide, I+prosulfocarb, I+prosulfuron, I+pyraclonil, I+pyraflufen, I+pyraflufen-ethyl, I+pyrasulfotole, I+pyrazolynate, I+pyrazosulfuron, I+pyrazosulfuron-ethyl, I+pyrazoxyfen, I+pyribenzoxim, I+pyributicarb, I+pyridafol, I+pyridate, I+pyriftalid, I+pyriminobac, I+pyriminobac-methyl, I+pyrimisulfan, I+pyrithiobac, I+pyrithiobac-sodium, I+pyroxasulfone, I+pyroxsulam, I+quinclorac, I+quinmerac, I+quinoclamine, I+quizalofop, I+quizalofop-P, I+rimsulfuron, I+saflufenacil, I+sethoxydim, I+siduron, I+simazine, I+simetryn, I+sodium chlorate, I+sulcotrione, I+sulfentrazone, I+sulfometuron, I+sulfometuron-methyl, I+sulfosate, I+sulfosulfuron, I+sulfuric acid, I+tebuthiuron, I+tefuryltrione, I+tembotrione, I+tepraloxydim, I+terbacil, I+terbumeton, I+terbuthylazine, I+terbutryn, I+thenylchlor, I+thiazopyr, I+thifensulfuron, I+thiencarbazone, I+thifensulfuron-methyl, I+thiobencarb, I+topramezone, I+tralkoxydim, I+triallate, I+triasulfuron, I+triaziflam, I+tribenuron, I+tribenuron-methyl, I+triclopyr, I+trietazine, I+trifloxysulfuron, I+trifloxysulfuron-sodium, I+trifluralin, I+triflusulfuron, I+triflusulfuron-methyl, I+trihydroxytriazine, I+trinexapac-ethyl, I+tritosulfuron, I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6). The compounds of the present invention may also be combined with herbicidal compounds disclosed in WO06/024820 and/or WO07/096576.

The mixing partners of the compound of Formula I may also be in the form of esters or salts, as mentioned e.g. in The Pesticide Manual, Fourteenth Edition, British Crop Protection Council, 2006.

The compound of Formula I can also be used in mixtures with other agrochemicals such as fungicides, nematicides or insecticides, examples of which are given in The Pesticide Manual.

The mixing ratio of the compound of Formula I to the mixing partner is preferably from 1:100 to 1000:1.

The mixtures can advantageously be used in the above-mentioned formulations (in which case "active ingredient" relates to the respective mixture of compound of Formula I with the mixing partner).

The compounds of Formula I according to the invention can also be used in combination with one or more safeners. Likewise, mixtures of a compound of Formula I according to the invention with one or more further herbicides can also be used in combination with one or more safeners. The safeners can be AD 67 (MON 4660), benoxacor, cloquintocet-mexyl, cyprosulfamide (CAS RN 221667-31-8), dichlormid, fenchlorazole-ethyl, fenclorim, fluxofenim, furilazole and the corresponding R isomer, isoxadifen-ethyl, mefenpyr-diethyl, oxabetrinil, N-isopropyl-4-(2-methoxy-benzoylsulfamoyl)-benzamide (CAS RN 221668-34-4). Other possibilities include safener compounds disclosed in, for example, EP0365484 e.g N-(2-methoxybenzoyl)-4-[(methylaminocarbonyl)amino]benzenesulfonamide. Particularly preferred are mixtures of a compound of Formula I with cyprosulfamide, isoxadifen-ethyl, cloquintocet-mexyl and/or N-(2-methoxybenzoyl)-4-[(methyl-aminocarbonyl)amino] benzenesulfonamide.

The safeners of the compound of Formula I may also be in the form of esters or salts, as mentioned e.g. in The Pesticide Manual, 14$^{th}$ Edition (BCPC), 2006. The reference to cloquintocet-mexyl also applies to a lithium, sodium, potassium, calcium, magnesium, aluminium, iron, ammonium, quaternary ammonium, sulfonium or phos-phonium salt thereof as disclosed in WO 02/34048, and the reference to fenchlorazole-ethyl also applies to fenchlorazole, etc.

Preferably the mixing ratio of compound of Formula I to safener is from 100:1 to 1:10, especially from 20:1 to 1:1.

The mixtures can advantageously be used in the above-mentioned formulations (in which case "active ingredient" relates to the respective mixture of compound of Formula I with the safener).

The present invention still further provides a method of selectively controlling weeds at a locus comprising crop plants and weeds, wherein the method comprises application to the locus of a weed controlling amount of a composition according to the present invention. 'Controlling' means killing, reducing or retarding growth or preventing or reducing germination. Generally the plants to be controlled are unwanted plants (weeds). 'Locus' means the area in which the plants are growing or will grow.

The rates of application of compounds of Formula I may vary within wide limits and depend on the nature of the soil, the method of application (pre- or post-emergence; seed dressing; application to the seed furrow; no tillage application etc.), the crop plant, the weed(s) to be controlled, the prevailing climatic conditions, and other factors governed by the method of application, the time of application and the target crop. The compounds of Formula I according to the invention are generally applied at a rate of from 10 to 2000 g/ha, especially from 50 to 1000 g/ha.

The application is generally made by spraying the composition, typically by tractor mounted sprayer for large areas, but other methods such as dusting (for powders), drip or drench can also be used.

Useful plants in which the composition according to the invention can be used include crops such as cereals, for example barley and wheat, cotton, oilseed rape, sunflower, maize, rice, soybeans, sugar beet, sugar cane and turf. Some of the compounds of the present invention have a particularly useful utility in controlling weeds in soybean.

Crop plants can also include trees, such as fruit trees, palm trees, coconut trees or other nuts. Also included are vines such as grapes, fruit bushes, fruit plants and vegetables.

Crops are to be understood as also including those crops which have been rendered tolerant to herbicides or classes of herbicides (e.g. ALS-, GS-, EPSPS-, PPO-, ACCase- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

In a preferred embodiment the crop plant is rendered tolerant to HPPD-inhibitors via genetic engineering. Methods of rending crop plants tolerant to HPPD-inhibitors are known, for example from WO0246387. Thus in an even more preferred embodiment the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria*, *Chenchrus*, *Lolium*, *Festuca*, *Setaria*, *Eleusine*, *Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), Nature-Gard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Other useful plants include turf grass for example in golf-courses, lawns, parks and roadsides, or grown commercially for sod, and ornamental plants such as flowers or bushes.

The compositions can be used to control unwanted plants (collectively, 'weeds'). The weeds to be controlled may be both monocotyledonous species, for example *Agrostis*, *Alopecurus*, *Avena*, *Brachiaria*, *Bromus*, *Cenchrus*, *Cyperus*, *Digitaria*, *Echinochloa*, *Eleusine*, *Lolium*, *Monochoria*, *Rottboellia*, *Sagittaria*, *Scirpus*, *Setaria* and *Sorghum*, and dicotyledonous species, for example *Abutilon*, *Amaranthus*, *Ambrosia*, *Chenopodium*, *Chrysanthemum*, *Conyza*, *Galium*, *Ipomoea*, *Nasturtium*, *Sida*, *Sinapis*, *Solanum*, *Stellaria*, *Veronica*, *Viola* and *Xanthium*. Weeds can also include plants which may be considered crop plants but which are growing outside a crop area ('escapes'), or which grow from seed left over from a previous planting of a different crop (volunteers'). Such volunteers or escapes may be tolerant to certain other herbicides.

The compounds of the present invention can be prepared according to schemes 1 and 2 below.

Scheme 1:- Reaction of an activated carboxylic acid:

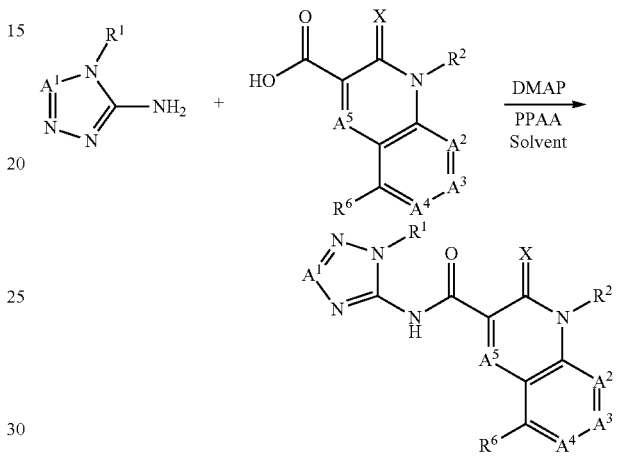

DMAP=4-dimethylaminopyridine, PPAA=1-propanephosphonic acid cyclic anhydride, and the solvent is a non-protic organic solvent such as ethyl acetate.

Scheme 2:- Reaction of carboxylic ester with an aminotetrazole or an aminotriazole under microwave conditions:

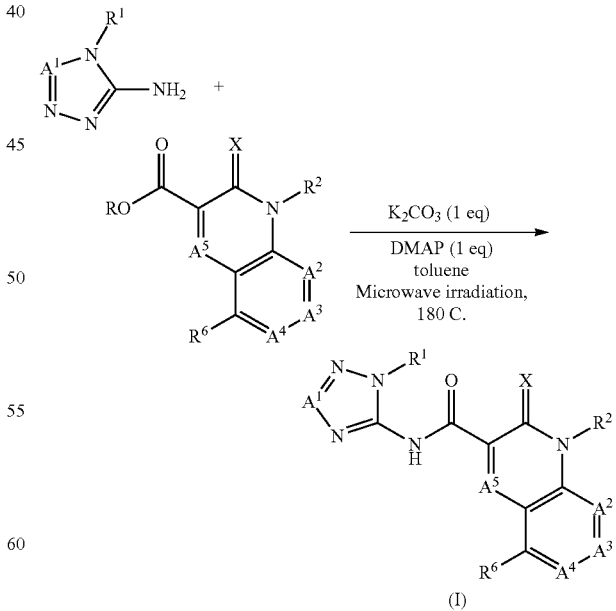

The carboxylic acids and esters are known, or can be prepared by known methods or methods analogous to known methods. In cases where $R^2$ is (substituted)aryl or (substituted)heteroaryl, this can be coupled to an NH-heterocycle by the method according to scheme 3.

Scheme 3:- Coupling of a (substituted) aryl- or heteroaryl-boronic acid to an NH-heterocycle:

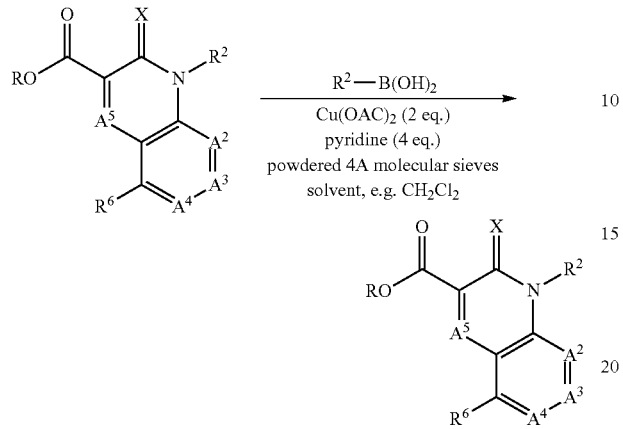

The following non-limiting examples provide specific synthesis methods for representative compounds of the present invention, as referred to in Tables 1 to 9 below.

EXAMPLE P1

Experimental Procedure for the Preparation of Compound 5.015

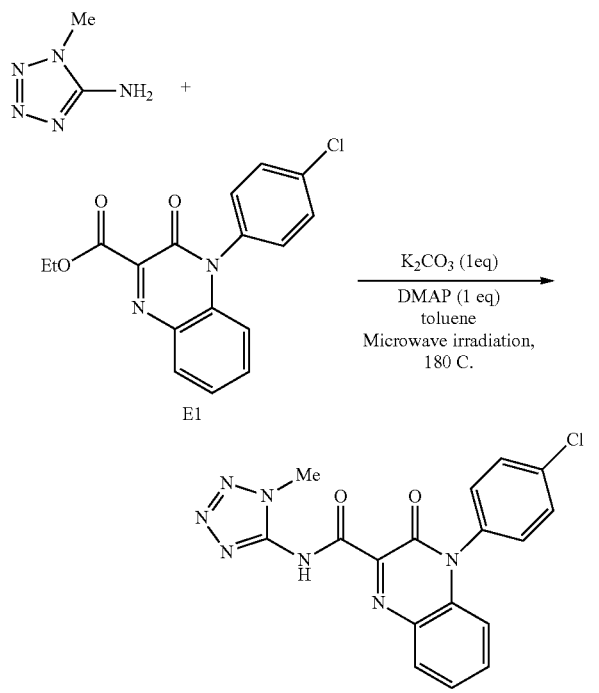

To a microwave vial (2-5 ml capacity) containing a magnetic stirrer bar were added ethyl 4-(4-chlorophenyl)-3-oxo-quinoxaline-2-carboxylate (E1, 265 mg, 0.265 g, 0.8061 mmol) and 5-amino-1-methyltetrazole (1 equiv., 0.0799 g, 0.8061 mmol) followed by anhydrous toluene (3 mL) then potassium carbonate (1 equiv., 0.11303 g, 0.8061 mmol) and DMAP N,N-dimethylaminopyridine (1 equiv., 0.098481 g, 0.8061 mmol). This mixture was stirred well, and then the vial was sealed and irradiated in a microwave at 180° C. for 45 min. The pressure rose to 2 bars. The reaction mixture was then evaporated under reduced pressure and the residue was purified using the CombiFlash Rf purification system from Presearch using a 12 g Redisep pre-packed and solid load cartridge (not a Gold column). The eluant system used was a gradient dichloromethane/methanol, 0% to 50%. The pure product was obtained as a yellow powder (223 mg; 72% yield).

EXAMPLE P2

Experimental Procedure for the Preparation of Compound 5.019

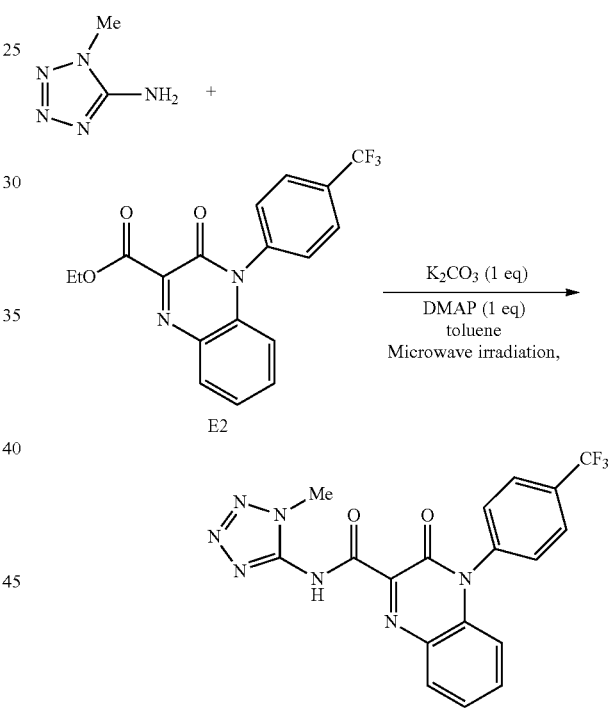

To a microwave vial (2-5 ml capacity) containing a magnetic stirrer bar were added ethyl 3-oxo-4-[4-(trifluoromethyl)phenyl]quinoxaline-2-carboxylate (E2, 170 mg, 0.17 g, 0.4692 mmol) and 5-amino-1-methyltetrazole (1 equiv., 0.0465 g, 0.4692 mmol) followed by anhydrous toluene (3 mL) then potassium carbonate (1 equiv., 0.065791 g, 0.4692 mmol) and DMAP N,N-dimethylaminopyridine (1 equiv., 0.057322 g, 0.4692 mmol). The mixture was stirred well, and then the vial was sealed and irradiated in the microwave at 180° C. for 45 min (twice), when all the starting material had been consumed. The reaction mixture was then evaporated under reduced pressure and the residue was purified using the CombiFlash Rf purification system from Presearch using a 12 g Redisep pre-packed and solid load cartridge (not a Gold column). The eluant system used was a gradient dichloromethane/methanol, 0% to 50%. The pure product was isolated as a yellow powder (160 mg; 82% yield).

EXAMPLE P3

Experimental Procedure for the Preparation of Compound 5.039

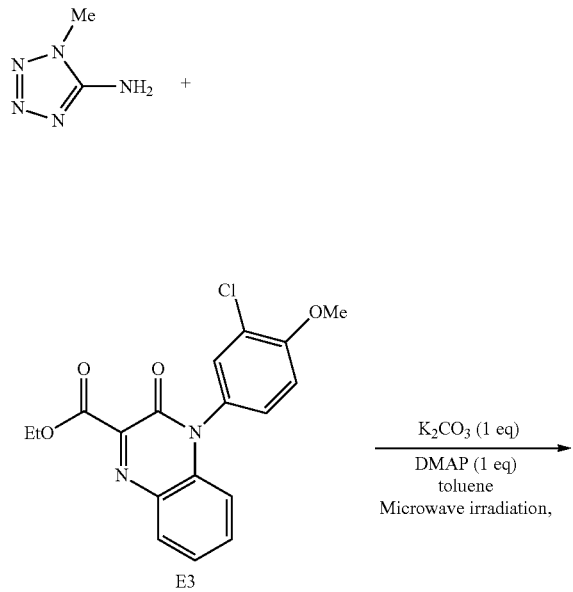

To a microwave vial (2-5 ml capacity) containing a magnetic stirrer bar were added ethyl 4-(3-chloro-4-methoxyphenyl)-3-oxo-quinoxaline-2-carboxylate (E3, 145 mg, 0.145 g, 0.4041 mmol) and 5-amino-1-methyltetrazole (1 equiv., 0.04 g, 0.4041 mmol) followed by anhydrous toluene (2 mL) then potassium carbonate (1 equiv., 0.056663 g, 0.4041 mmol) and DMAP N,N-dimethylaminopyridine (1 equiv., 0.049369 g, 0.4041 mmol). This mixture was stirred well, and then the vial was sealed and irradiated in the microwave at 180° C. for 45 min. Ethyl acetate was added to the reaction mixture, and the mixture was then filtered. The organic phase was discarded and the insoluble solid was purified using the CombiFlash Rf purification system from Presearch using a 12 g Redisep pre-packed and solid load cartridge (not a Gold column). The eluant system used was a gradient dichloromethane/methanol, 0% to 40%. The pure product was isolated as a yellow powder (105 mg; 63% yield).

EXAMPLE P4

Experimental Procedure for the Preparation of E5

To a round bottom flask equipped with a magnetic stirrer bar were introduced ethyl 3-oxo-4H-quinoxaline-2-carboxylate (E4, 150 mg, 0.15 g, 0.68741 mmol) and [3-(trifluoromethyl)phenyl]boronic acid (2 equiv., 0.26112 g, 1.3748 mmol) in dichloromethane (12 mL) followed by powdered molecular sieves (4A, 75 mg, 0.075 g), pyridine (4 equiv., 0.21750 g, 2.7496 mmol) and finally copper (II) acetate (2 equiv., 0.24971 g, 1.3748 mmol). The reaction mixture was stirred at room temperature until all the starting material E4 had been consumed. Ethyl acetate was added, and the resultant mixture was filtered through Hyflow, the copper salts were rinsed with more ethyl acetate, and then the green organic phase was concentrated under reduced pressure. The crude material was purified using the CombiFlash Rf purification system from Presearch using a 12 g Redisep pre-packed and solid load cartridge (not a Gold column). The eluant system used was a gradient iso-hexane/ethyl acetate, 0% to 100%. The product was isolated as a yellow powder (180 mg, 72% yield).

EXAMPLE P5

Experimental Procedure for the Preparation of E6

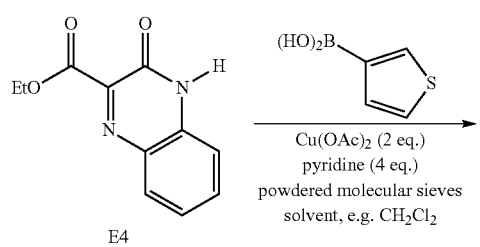

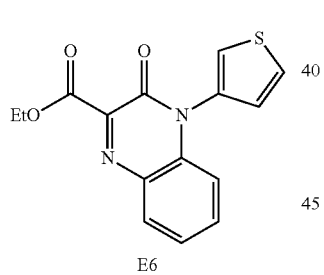

To a round bottom flask equipped with a magnetic stirrer bar were introduced ethyl 3-oxo-4H-quinoxaline-2-carboxylate (E4, 200 mg, 0.2 g, 0.91655 mmol), 3-thienylboronic acid (2 equiv., 0.23456 g, 1.8331 mmol) and dichloromethane (10 mL). The mixture was stirred well before adding powdered molecular sieves (4A, 100 mg, 0.1 g), pyridine (4 equiv., 0.29000 g, 3.6662 mmol) and copper (II) acetate (1.35 equiv., 0.22474 g, 1.2373 mmol). The reaction mixture was stirred at room temperature until most of the starting material E4 had been consumed, adding more 3-thienylboronic acid along the way. The reaction mixture was then diluted with dichloromethane and filtered through Hyflow, washing the residual copper salts with more dichloromethane, then the organic phase was evaporated to dryness under reduced pressure. The solid residue was purified using the CombiFlash Rf purification system from Presearch using a 24 g Redisep pre-packed and solid load cartridge (not a Gold column). The eluant system used was a gradient iso-hexane/ethyl acetate, 0% to 100%. The product E6 was isolated as a pale yellow solid (145 mg, 53% yield).

EXAMPLE P6

Experimental Procedure for the Preparation of E8

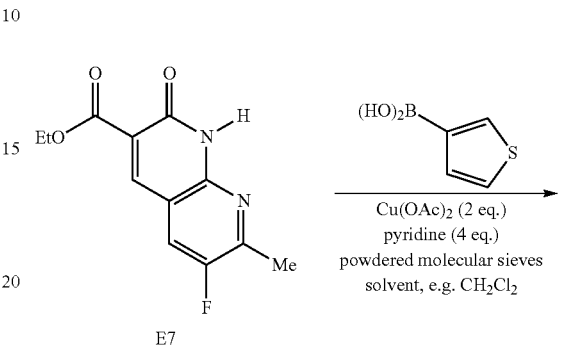

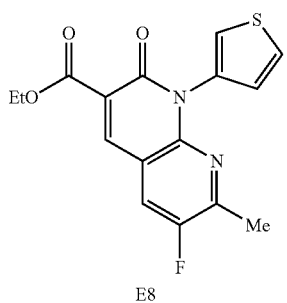

To a round bottom flask equipped with a magnetic stirrer bar were introduced ethyl 6-fluoro-7-methyl-2-oxo-1H-1,8-naphthyridine-3-carboxylate (E7, 290 mg, 0.29 g, 1.1589 mmol), 3-thienylboronic acid (2 equiv., 0.29659 g, 2.3179 mmol) and dichloromethane (10 mL). The mixture was stirred well before adding powdered molecular sieves (4A, 100 mg, 0.1 g), pyridine (4 equiv., 0.36670 g, 4.6357 mmol) and copper (II) acetate (2 equiv., 0.42099 g, 2.3179 mmol). The reaction mixture was stirred at room temperature until all starting material E7 had been consumed. The reaction mixture was then diluted with dichloromethane and filtered through Hyflow, washing the residual copper salts with more dichloromethane, then the green organic phase was evaporated to dryness under reduced pressure. The solid residue was purified using the CombiFlash Rf purification system from Presearch using a 24 g Redisep pre-packed and solid load cartridge (not a Gold column). The eluant system used was a gradient iso-hexane/ethyl acetate, 0% to 100%. The product E8 was isolated as a pale yellow powder (168 mg, 44% yield).

TABLE 1

Examples of herbicidal compounds of the present invention.

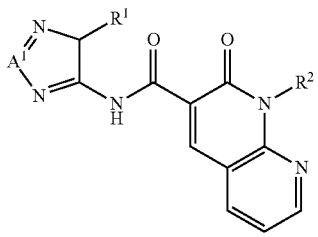

| Compound | R¹ | R² | A¹ | NMR |
|---|---|---|---|---|
| 1.001 | Me | Me | N | δ6-DMSO: 8.58 (1H, dd), 8.16 (1H, dd), 7.85 (1H, s), 7.28 (1H, dd), 3.68 (3H, s), 3.67 (3H, s). |
| 1.002 | Me | phenyl | N | |
| 1.003 | Et | phenyl | N | |
| 1.004 | Me | 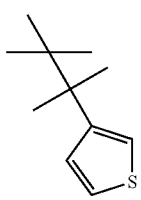 | N | |
| 1.005 | Me | 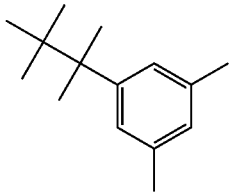 | N | |
| 1.006 | Me | 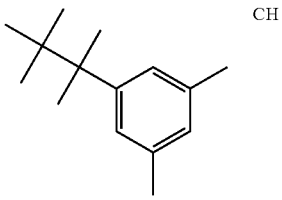 | CH | |

TABLE 2

Examples of herbicidal compounds of the present invention.

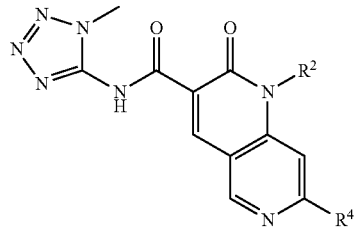

| Compound | R² | R⁴ | NMR |
|---|---|---|---|
| 2.001 | phenyl | Cl | δ6-DMSO: 11.62 (1H, bs), 9.22 (1H, s), 9.19 (1H, s), 7.63-7.72 (3H, m), 7.50 (2H, m), 6.47 (1H, s), 3.93 (3H, s). |

TABLE 2-continued

Examples of herbicidal compounds of the present invention.

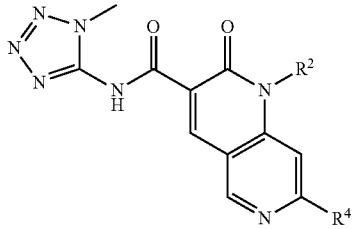

| Compound | R² | R⁴ | NMR |
|---|---|---|---|
| 2.002 | Et | Cl | δ6-DMSO: 11.85 (1H, bs), 9.11 (1H, s), 9.08 (1H, s), 7.92 (1H, s), 4.38 (2H, q), 1.27 (3H, t). |
| 2.003 | Et | H | δ6-DMSO: 12.00 (1H, bs), 9.26 (1H, s), 9.10 (1H, s), 8.77 (1H, d), 7.75 (1H, d), 4.40 (2H, q), 3.97 (3H, s), 1.30 (3H, t). |

TABLE 3

Examples of herbicidal compounds of the present invention.

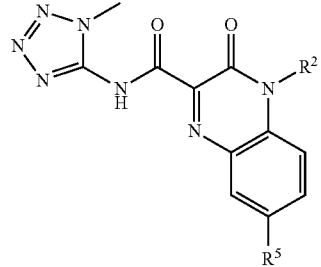

| Compound | R² | R⁵ | NMR |
|---|---|---|---|
| 3.001 | Me | —CF₃ | CDCl₃: 12.23 (1H, bs), 8.56 (1H, s), 8.04 (1H, dd), 7.63 (1H, d), 4.14 (3H, s), 3.92 (3H, s). |

TABLE 4

Examples of herbicidal compounds of the present invention.

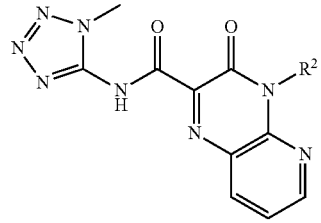

| Compound | R² | NMR |
|---|---|---|
| 4.001 | Me | δ6-DMSO: 8.73 (1H, s), 8.34 (1H, m), 7.52 (1H, m), 3.89 (3H, s), 3.71 (3H, s). |
| 4.002 | -phenyl | δ6-DMSO: 8.52 (1H, dd), 7.66 (2H, m), 7.59 (1H, m), 7.42 (3H, m), 7.00 (1H, dd), 3.66 (3H, s). |

TABLE 5

Examples of herbicidal compounds of the present invention.

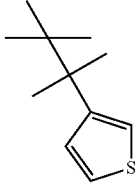

| Compound | A¹ | R² | R⁴ | R⁵ | NMR |
|---|---|---|---|---|---|
| 5.001 | N | Me | Br | H | δ6-DMSO: 12.26 (1H, bs), 9.02 (1H, s), 8.06 (1H, d), 7.98 (1H, s), 7.64 (1H, d), 3.96 (3H, s), 3.79 (3H, s). |
| 5.002 | N | Me | H | H | CDCl₃: 12.53 (1H, bs), 8.26 (1H, dd), 7.85 (1H, dt), 7.58 (1H, dt), 7.52 (1H, d), 4.14 (3H, s), 3.89 (3H, s). |
| 5.003 | N | 6-Me-pyridin-2-yl | H | H | δ6-DMSO: 11.95 (1H, bs), 8.08 (1H, t), 8.03 (1H, m), 7.61 (1H, t); 7.56 (1H, d), 7.49 (1H, m), 6.64 (1H, d), 3.97 (3H, s), 2.56 (3H, s) |
| 5.004 | N | -phenyl | H | H | δ6-DMSO: 11.94 (1H, bs), 8.04 (1H, m), 7.69 (2H, m), 7.62 (2H, m), 7.49 (3H, m), 6.68 (1H, d), 3.97 (3H, s). |
| 5.005 | N | (2-(thiophen-3-yl)propan-2-yl) | H | H | δ6-DMSO: 7.85 (1H, m), 7.79 (2H, m), 7.46 (1H, t), 7.35 (1H, t), 7.14 (1H, d), 6.74 (1H, d), 3.70 (3H, s). |
| 5.006 | N | -phenyl | —CF₃ | H | δ6-DMSO: 8.00 (1H, d), 7.60-7.71 (4H, m), 7.45 (2H, d), 6.71 (1H, s), 3.66 (3H, s). |
| 5.007 | N | -phenyl | H | Cl | δ6-DMSO: 7.92 (1H, d), 7.61-7.71 (3H, m), 7.40 (3H, m), 6.70 (1H, d), 3.89 (3H, s). |
| 5.008 | N | -phenyl | Cl | H | δ6-DMSO: 7.89 (1H, d), 7.61-7.71 (3H, m), 7.40 (3H, m), 6.66 (1H, d), 3.89 (3H, s). |
| 5.009 | N | 4-MeO-phenyl- | H | H | δ6-DMSO: 8.10 (2H, d), 7.35 (2H, m), 7.19 (2H, d), 6.60 (2H, d), 3.86 (3H, s). |
| 5.010 | N | -phenyl | F | H | CD₃OD: 8.16 (1H, t), 7.70 (3H, m), 7.44 (2H, d), 7.31 (1H, dt), 6.45 (1H, dd), 4.05 (3H, s). |
| 5.011 | N | 3-Me-phenyl- | H | H | CD₃OD: 7.70 (3H, m), 7.46-7.64 (4H, m), 7.20-7.25 (2H, m), 6.82 (1H, d), 4.05 (3H, s), 2.47 (3H, s). |
| 5.012 | N | 4-Me-phenyl- | H | H | CD₃OD: 8.11 (1H, d), 7.63 (1H, t), 7.51 (3H, m), 7.29 (2H, d), 6.84 (1H, d), 4.06 (3H, s), 2.50 (3H, s). |
| 5.013 | N | 3-furanyl- | H | H | CD₃OD: 8.05 (1H, m), 7.93 (1H, s), 7.84 (1H, s), 7.68 (1H, t), 7.51 (1H, d), 7.23 (1H, d), 6.66 (1H, s), 4.04 (3H, s). |
| 5.014 | N | 3-EtO-phenyl- | H | H | CDCl3: 12.37 (1H, bs, NH), 8.29 (1H, d), 7.64 (1H, t), 7.59 (1H, t), 7.54 (1H, t), 7.18 (1H, dd), 6.90 (2H, m), 6.84 (1H, m), 4.13 (3H, s), 4.10 (2H, q), 1.46 (3H, t). |
| 5.015 | N | 4-Cl-phenyl- | H | H | CDCl₃: 12.18 (1H, bs, NH), 8.27 (1H, d), 7.68 (2H, d), 7.65 (1H, t), 7.55 (1H, t), 7.31 (2H, d), 6.85 (1H, d), 4.11 (3H, s). |
| 5.016 | N | 3-Cl-phenyl- | H | H | CDCl₃: 12.17 (1H, bs, NH), 8.30 (1H, d), 7.67 (3H, m), 7.57 (1H, t), 7.38 (1H, s), 7.27 (1H, m), 6.86 (1H, d), 4.13 (3H, s). |
| 5.017 | N | 3,5-dichlorophenyl- | H | H | CDCl₃: 12.01 (1H, bs, NH), 8.30 (1H, d), 7.71 (1H, dt), 7.68 (1H, t), 7.59 (1H, dt), 7.30 (2H, d), 6.87 (1H, d), 4.13 (3H, s). |
| 5.018 | N | 3-F-phenyl- | H | H | CDCl₃: 12.19 (1H, bs, NH), 8.31 (1H, dd), 7.72 (1H, m), 7.67 (1H, dt) 7.57 (1H, dt), 7.40 (1H, dt), 7.16 (1H, d), 7.14 (1H, dt), 6.86 (1H, d), 4.13 (3H, s). |
| 5.019 | N | 4-CF₃-phenyl- | H | H | CDCl₃: 12.10 (1H, bs, NH), 8.32 (1H, dd), 8.00 (2H, d), 7.67 (1H, dt), 7.58 (1H, dt), 7.53 (2H, d), 6.81 (1H, d), 4.13 (3H, s). |
| 5.020 | N | 4-MeS-phenyl- | H | H | CDCl₃: 12.32 (1H, bs, NH), 8.29 (1H, d), 7.64 (1H, t), 7.54 (1H, t), 7.52 (2H, d), 7.25 (2H, d), 6.92 (1H, d), 4.12 (3H, s), 2.60 (3H, s). |
| 5.021 | N | 3-CN-phenyl- | H | H | CDCl₃: 11.94 (1H, bs, NH), 8.29 (1H, d), 7.97 (1H, d), 7.87 (1H, t), 7.67 (3H, m), 7.58 (1H, t), 6.76 (1H, d), 4.11 (3H, s). |

TABLE 5-continued

Examples of herbicidal compounds of the present invention.

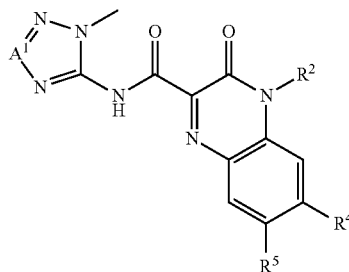

| Compound | A¹ | R² | R⁴ | R⁵ | NMR |
|---|---|---|---|---|---|
| 5.022 | N | 4-NO₂-phenyl- | H | H | CDCl₃: 11.96 (1H, bs, NH), 8.59 (2H, d), 8.32 (1H, d), 7.68 (1H, t), 7.60 (3H, m), 6.79 (1H, d), 4.13 (3H, s). |
| 5.023 | N | 3-Cl,4-F-phenyl- | H | H | CDCl₃: 12.08 (1H, bs, NH), 8.30 (1H, dd), 7.69 (1H, dt), 7.58 (1H, dt), 7.47 (2H, m), 7.29 (1H, m), 6.87 (1H, d), 4.13 (3H, s). |
| 5.024 | N | 3-Br-phenyl- | H | H | CDCl₃: 12.16 (1H, bs, NH), 8.27 (1H, d), 7.81 (1H, d), 7.66 (1H, t), 7.60 (1H, t), 7.55 (2H, m), 7.32 (1H, d), 6.85 (1H, d), 4.11 (3H, s). |
| 5.025 | N | 3-NO₂-phenyl- | H | H | CDCl₃: 11.96 (1H, bs, NH), 8.55 (1H, d), 8.32 (2H, m), 7.95 (1H, t), 7.76 (1H, d), 7.68 (1H, t), 7.59 (1H, t), 6.80 (1H, d), 4.12 (3H, s). |
| 5.026 | N | 3-CF₃-phenyl- | H | H | CDCl₃: 12.09 (1H, bs, NH), 8.31 (1H, dd), 7.95 (1H, d), 7.88 (1H, t), 7.66 (2H, m), 7.59 (2H, m), 6.80 (1H, d), 4.12 (3H, s). |
| 5.027 | N | 3-vinyl-phenyl- | H | H | CDCl₃: 12.33 (1H, bs, NH), 8.30 (1H, dd), 7.67 (3H, m), 7.55 (1H, t), 7.37 (1H, s), 7.22 (1H, m), 6.90 (1H, d), 6.79 (1H, dd), 5.85 (1H, d), 5.43 (1H, d), 4.13 (3H, s). |
| 5.028 | N | 3-Me,4-F-phenyl- | H | H | CDCl₃: 12.27 (1H, bs, NH), 8.27 (1H, dd), 7.65 (1H, dt), 7.55 (1H, dt), 7.33 (1H, t), 7.16 (2H, m), 6.88 (1H, d), 4.11 (3H, s), 2.40 (3H, d). |
| 5.029 | N | 4-F-phenyl- | H | H | CDCl₃: 12.22 (1H, bs, NH), 8.28 (1H, d), 7.65 (1H, t), 7.55 (1H, t), 7.38 (4H, m), 8.65 (1H, d), 4.12 (3H, s). |
| 5.030 | N | 4-CF₃O-phenyl- | H | H | CDCl₃: 12.16 (1H, bs, NH), 8.30 (1H, dd), 7.67 (1H, d), 7.57 (3H, m), 7.42 (2H, d), 6.84 (1H, d), 4.12 (3H, s). |
| 5.031 | N | 2-naphthyl- | H | H | CDCl₃: 12.35 (1H, bs, NH), 8.32 (1H, dd), 8.18 (1H, d), 8.03 (1H, d), 7.95 (1H, d), 7.88 (1H, d), 7.53-7.71 (4H, m), 7.38 (1H, dd), 6.90 (1H, dd), 4.13 (3H, s). |
| 5.032 | N | 4-Br-phenyl- | H | H | CDCl₃: 12.19 (1H, bs, NH), 8.30 (1H, d), 7.85 (2H, d), 7.66 (1H, t), 7.56 (1H, t), 7.24 (2H, d), 6.86 (1H, d), 4.13 (3H, s). |
| 5.033 | N | 3-F,4-MeO-phenyl | H | H | CDCl₃: 12.25 (1H, bs, NH), 8.30 (1H, d), 7.66 (1H, t), 7.56 (1H, t), 7.25 (1H, m), 7.11 (1H, m), 6.92 (1H, d), 4.13 (3H, s), 4.04 (3H, s). |
| 5.034 | N | 2-Me-phenyl | H | H | CDCl₃: 12.39 (1H, bs, NH), 8.31 (1H, d), 7.64 (1H, t), 7.50-7.60 (3H, m), 7.31 (1H, t), 7.20 (1H, m), 6.76 (1H, d), 4.13 (3H, s), 2.07 (3H, s). |
| 5.035 | N | 3,4 diclorophenyl | H | H | CDCl₃: 12.07 (1H, bs, NH), 8.30 (1H, dd), 7.80 (1H, d), 7.69 (1H, t), 7.58 (1H, t), 7.50 (1H, d), 7.24 (1H, dd), 6.88 (1H, d), 4.13 (3H, s). |
| 5.036 | N | 3-Me,4-Cl-phenyl | H | H | CDCl₃: 12.24 (1H, bs, NH), 8.29 (1H, dd), 7.68 (1H, d), 7.65 (1H, dt), 7.56 (1H, dt), 7.23 (1H, d), 7.14 (1H, dd), 6.89 (1H, d), 4.12 (3H, s), 2.51 (3H, s). |
| 5.037 | N | 3-CF₃,4-Cl-phenyl | H | H | CDCl₃: 11.98 (1H, bs, NH), 8.30 (1H, dd), 7.87 (1H, d), 7.73 (1H, d), 7.69 (1H, t), 7.58 (1H, t), 7.54 (1H, dd), 6.81 (1H, d), 4.11 (3H, s). |
| 5.038 | CH | 6-Me-pyridin-2-yl | H | H | CDCl₃: 11.84 (1H, bs, NH), 8.28 (1H, d), 7.98 (1H, t), 7.81 (1H, s), 7.60 (1H, t), 7.52 (1H, d), 7.47 (2H, m), 6.71 (1H, d), 3.89 (3H, s), 2.69 (3H, s). |
| 5.039 | N | 3-Cl,4-MeO-phenyl- | H | H | CDCl₃: 12.24 (1H, bs, NH), 8.27 (1H, d), 7.66 (1H, t), 7.55 (1H, t), 7.38 (1H, d), 7.23 (2H, m), 6.92 (1H, d), 4.12 (3H, s), 4.04 (3H, s). |
| 5.040 | N | 3-Cl,4-CF₃-phenyl- | H | H | CDCl₃: 11.96 (1H, bs, NH), 8.30 (1H, d), 8.06 (1H, d), 7.70 (1H, t), 7.59 (2H, m), 7.44 (1H, d), 6.83 (1H, d), 4.12 (3H, s). |
| 5.041 | CH | Phenyl- | H | H | CDCl₃: 11.95 (1H, bs, NH), 8.29 (1H, d), 7.81 (1H, s), 7.70 (3H, m), 7.60 (1H, t), 7.52 (1H, t), 7.34 (2H, d), 6.82 (1H, d), 3.90 (3H, s). |
| 5.042 | N | 4-I-phenyl- | H | H | CDCl₃: 12.20 (1H, bs, NH), 8.30 (1H, d), 8.05 (2H, d), 7.66 (1H, t), 7.56 (1H, t), 7.10 (2H, d), 6.87 (1H, d), 4.13 (3H, s). |
| 5.045 | N | 3-CF₃,5-CF₃-phenyl | H | H | (DMSO) 8.34 (3H, m), 7.81 (1H, dd), 7.34-7.43 (2H, m), 6.60 (1H, dd), 3.66 (3H, s). |

TABLE 5-continued

Examples of herbicidal compounds of the present invention.

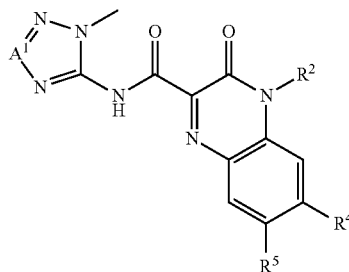

| Compound | A¹ | R² | R⁴ | R⁵ | NMR |
|---|---|---|---|---|---|
| 5.043 | N | Phenyl- | Me | Me | (CDCl$_3$) 12.41(1H, bs), 8.04 (1H, s), 7.71 (3H, m), 7.33 (2H, m), 6.58 (1H, s), 4.12 (3H, s), 2.41 (3H, s), 2.33 (3H, s). |
| 5.044 | N | Phenyl- | NO$_2$ | H | (CDCl$_3$) 12.02 (1H, bs), 8.46 (1H, d), 7.34-7.78 (7H, m), 4.13 (3H, s). |
| 5.045 | N | Phenyl- | H | NO$_2$ | |
| 5.046 | N | Phenyl- | H | F | (CDCl$_3$) 12.29 (1H, bs), 7.99 (1H, dd), 7.73 (3H, m), 7.39 (1H, m), 7.34 (2H, m), 6.86 (1H, dd), 4.13 (3H, s). |
| 5.047 | N | 3-I-phenyl- | H | H | (DMSO) 7.96 (1H, d), 7.76-7.81 (2H, m), 7.39-7.46 (3H, m), 7.33 (1H, t), 6.57 (1H, d), 3.65 (3H, s). |

TABLE 6

Examples of herbicidal compounds of the present invention.

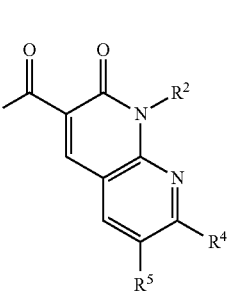

| Compound | R² | R⁴ | R⁵ | NMR |
|---|---|---|---|---|
| 6.001 | -phenyl | H | F | δ6-DMSO: 8.37 (1H, d), 8.21 (1H, dd), 7.95 (1H, s), 7.53 (2H, m), 7.44 (1H, m), 7.23 (2H, m), 3.63 (3H, s). |
| 6.002 | (2-methyl-2-(thiophen-3-yl)propyl) | Me | F | δ6-DMSO: 8.10 (1H, d), 7.90 (1H, s), 7.63 (1H, dd), 7.49 (1H, m), 7.01 (1H, m), 3.64 (3H, s), 2.34 (3H, d). |
| 6.003 | -phenyl | Me | F | δ6-DMSO: 8.12 (1H, d), 7.96 (1H, s), 7.52 (2H, m), 7.44 (1H, m), 7.22 (2H, m), 3.63 (3H, s), 2.28 (3H, d). |

TABLE 7

Examples of herbicidal compounds of the present invention.

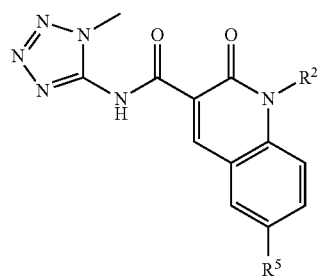

| Compound | R² | R⁵ | NMR |
|---|---|---|---|
| 7.001 | -phenyl | H | δ6-DMSO: 8.00 (1H, s), 7.78 (1H, d), 7.63 (2H, m), 7.54 (1H, m), 7.35 (1H, m), 7.29 (1H, m), 7.14-7.25 (2H, m), 6.44 (1H, d), 3.64 (3H, s). |
| 7.002 | (2-methyl-2-(thiophen-3-yl)propyl) | H | δ6-DMSO: 7.94 (1H, s), 7.80 (1H, dd), 7.76 (1H, dd), 7.65 (1H, dd), 7.39 (1H, t), 7.21 (1H, t), 7.06 (1H, dd), 6.62 (1H, d), 3.64 (3H, s). |

TABLE 8

Examples of herbicidal compounds of the present invention.

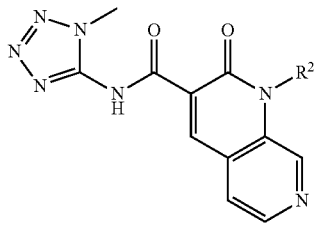

| Compound | R² | NMR |
|---|---|---|
| 8.001 | -phenyl | δ6-DMSO: 11.96 (1H, bs), 9.16 (1H, s), 8.10 (1H, d), 8.04 (1H, d), 8.00 (1H, s), 7.65 (3H, m), 7.52 (2H, m), 3.94 (3H, s) |

TABLE 9

Examples of herbicidal compounds of the present invention.

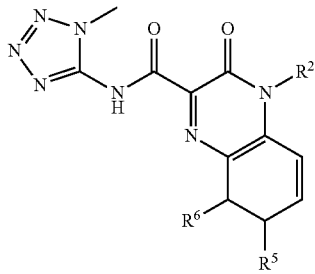

| Compound | R² | R⁵ | R⁶ | NMR |
|---|---|---|---|---|
| 9.001 | -phenyl | Me | Me | (CDCl₃) 12.35 (1H, bs), 7.69 (3H, m), 7.41 (1H, d), 7.31 (2H, m), 6.56 (1H, d), 4.14 (3H, s), 2.83 (3H, s), 2.44 (3H, s). |
| 9.002 | -phenyl | H | Cl | (CDCl₃) 11.91 (1H, bs), 7.70 (3H, m), 7.61 (1H, dd), 7.51 (1H, t), 7.32 (2H, m), 6.74 (1H, dd), 4.15 (3H, s). |
| 9.003 | 4-methoxyphenyl- | H | Cl | |

TABLE 9-continued

Examples of herbicidal compounds of the present invention.

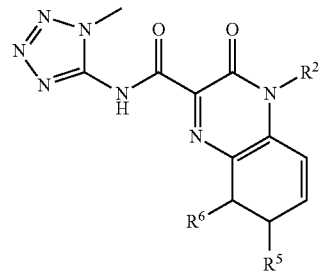

| Compound | R² | R⁵ | R⁶ | NMR |
|---|---|---|---|---|
| 9.004 | -phenyl | H | Me | (CDCl₃) 12.26 (1H, bs, NH), 7.70 (3H, m), 7.50 (1H, t), 7.38 (1H, d), 7.32 (2H, m), 6.65 (1H, d), 4.14 (3H, s), 2.90 (3H, s). |

BIOLOGICAL EXAMPLES

Seeds of a variety of test species are sown in standard soil in pots (*Alopecurus myosuroides* (ALOMY), *Setaria faberi* (SETFA), *Echinochloa crus-galli* (ECHCG), *Solanum nigrum* (SOLNI), *Amaranthus retoflexus* (AMARE), *Ipomoea hederacea* (IPOHE)). After cultivation for one day (pre-emergence) or after 8 days cultivation (post-emergence) under controlled conditions in a glasshouse (at 24/16° C., day/night; 14 hours light; 65% humidity), the plants are sprayed with an aqueous spray solution derived from the formulation of the technical active ingredient in acetone/water (50:50) solution containing 0.5% Tween 20 (polyoxyethelyene sorbitan monolaurate, CAS RN 9005-64-5). Compounds ae applied at 1000 g/h. The test plants are then grown in a glasshouse under controlled conditions in a glasshouse (at 24/16° C., day/night; 14 hours light; 65% humidity) and watered twice daily. After 13 days for pre and post-emergence, the test is evaluated for the percentage damage caused to the plant. The biological activities are shown in the following table on a five point scale (5=80-100%; 4=60-79%; 3=40-59%; 2=20-39%; 1=0-19%).

| | POST Application | | | | | | PRE Application | | | | | |
|---|---|---|---|---|---|---|---|---|---|---|---|---|
| Compound | SOLNI | AMARE | SETFA | ALOMY | ECHCG | IPOHE | SOLNI | AMARE | SETFA | ALOMY | ECHCG | IPOHE |
| 1.001 | 5 | 3 | 1 | 1 | 3 | 2 | 2 | 2 | 1 | 1 | 1 | 1 |
| 2.001 | 5 | 5 | 1 | 1 | 1 | 5 | 4 | 5 | 1 | 1 | 1 | 2 |
| 2.002 | 5 | 5 | 1 | 1 | 2 | 5 | 4 | 5 | 1 | 1 | 2 | 3 |
| 2.003 | 3 | 3 | 1 | 1 | 1 | 2 | 1 | 1 | 1 | 1 | 1 | 1 |
| 3.001 | 4 | 4 | 2 | 1 | 2 | 3 | 3 | 2 | 1 | 1 | 2 | 1 |
| 4.001 | 5 | 5 | 2 | 1 | 5 | 4 | 5 | 5 | 1 | 1 | 4 | 3 |
| 4.002 | 3 | 2 | 1 | 1 | 1 | 1 | 1 | 1 | 1 | 1 | 1 | 1 |
| 5.002 | 5 | 5 | 1 | 1 | 4 | 5 | 5 | 5 | 1 | 1 | 5 | 5 |
| 5.003 | 5 | 5 | 5 | 5 | 5 | 5 | 5 | 5 | 5 | 5 | 5 | 5 |
| 5.004 | 5 | 5 | 2 | 2 | 3 | 5 | 5 | 5 | 4 | 3 | 5 | 5 |
| 5.005 | 5 | 5 | 5 | 2 | 5 | 5 | 5 | 5 | 3 | 2 | 5 | 5 |
| 5.006 | 5 | 5 | 4 | 3 | 4 | 5 | 5 | 5 | 3 | 3 | 4 | 4 |
| 5.007 | 5 | 5 | 5 | 2 | 2 | 5 | 5 | 5 | 5 | 2 | 2 | 5 |
| 5.008 | 5 | 5 | 5 | 2 | 2 | 5 | 5 | 5 | 5 | 2 | 2 | 5 |
| 5.009 | 5 | 5 | 2 | 1 | 4 | 3 | 5 | 5 | 1 | 2 | 5 | 5 |
| 5.010** | 5 | 5 | 4 | 1 | 3 | 5 | 4 | 5 | 1 | 1 | 1 | 2 |
| 5.011 | 5 | 5 | 5 | 2 | 4 | 5 | 5 | 5 | 4 | 2 | 4 | 5 |
| 5.012 | 5 | 5 | 4 | 2 | 5 | 5 | 5 | 5 | 3 | 2 | 5 | 5 |
| 5.013** | 5 | 5 | 1 | 1 | 1 | 4 | 5 | 5 | 2 | 1 | 2 | 4 |
| 5.014 | 5 | 5 | 5 | 3 | 4 | 5 | 5 | 5 | 5 | 2 | 2 | 4 |
| 5.015 | 5 | 5 | 5 | 4 | 5 | 5 | 5 | 5 | 5 | 2 | 5 | 5 |

-continued

|         | POST Application | | | | | | PRE Application | | | | | |
|---------|-------|-------|-------|-------|-------|-------|-------|-------|-------|-------|-------|-------|
| Compound | SOLNI | AMARE | SETFA | ALOMY | ECHCG | IPOHE | SOLNI | AMARE | SETFA | ALOMY | ECHCG | IPOHE |
| 5.016 | 5 | 5 | 5 | 5 | 5 | 5 | 5 | 5 | 5 | 4 | 5 | 5 |
| 5.017 | 5 | 5 | 5 | 5 | 2 | 4 | 5 | 5 | 5 | 4 | 1 | 4 |
| 5.018 | 5 | 5 | 5 | 5 | 5 | 5 | 5 | 5 | 5 | 5 | 5 | 5 |
| 5.019 | 5 | 5 | 5 | 3 | 5 | 5 | 5 | 5 | 5 | 4 | 5 | 5 |
| 5.020 | 5 | 5 | 2 | 5 | 5 | 5 | 5 | 5 | 1 | 1 | 3 | 3 |
| 5.021 | 5 | 5 | 5 | 4 | 2 | 5 | 5 | 5 | 5 | 5 | 5 | 5 |
| 5.022 | 5 | 5 | 4 | 2 | 4 | 5 | 5 | 5 | 5 | 3 | 5 | 4 |
| 5.024 | 5 | 5 | 5 | 5 | 5 | 4 | 5 | 5 | 5 | 5 | 5 | 5 |
| 5.025 | 5 | 5 | 5 | 5 | 5 | 4 | 5 | 5 | 2 | 2 | 3 | 4 |
| 5.026 | 5 | 5 | 5 | 5 | 5 | 5 | 5 | 5 | 5 | 5 | 5 | 5 |
| 5.027 | 5 | 5 | 5 | 5 | 5 | 5 | 5 | 5 | 5 | 5 | 5 | 5 |
| 5.028* | 5 | 5 | 5 | 4 | 5 | 5 | 5 | 5 | 5 | 3 | 5 | 5 |
| 5.029 | 5 | 5 | 5 | 4 | 5 | 5 | 5 | 5 | 5 | 5 | 5 | 5 |
| 5.030 | 5 | 5 | 5 | 5 | 5 | 5 | 5 | 5 | 5 | 5 | 5 | 5 |
| 5.031 | 5 | 5 | 1 | 1 | 1 | 3 | 5 | 5 | 1 | 1 | 1 | 1 |
| 5.032 | 5 | 5 | 5 | 2 | 3 | 5 | 5 | 5 | 5 | 4 | 4 | 5 |
| 5.033 | 5 | 5 | 4 | 1 | 5 | 5 | 5 | 5 | 1 | 2 | 5 | 5 |
| 5.034 | 5 | 5 | 5 | 4 | 5 | 5 | 5 | 5 | 5 | 5 | 5 | 5 |
| 5.035 | 5 | 5 | 4 | 2 | 2 | 5 | 5 | 5 | 5 | 3 | 2 | 5 |
| 5.036 | 5 | 5 | 4 | 2 | 5 | 5 | 5 | 5 | 4 | 3 | 3 | 5 |
| 5.037 | 5 | 5 | 5 | 4 | 5 | 5 | 5 | 5 | 5 | 4 | 2 | 5 |
| 5.038 | 5 | 5 | 5 | 5 | 2 | 5 | 5 | 5 | 4 | 4 | 1 | 3 |
| 5.039 | 5 | 5 | 1 | 1 | 3 | 5 | 5 | 5 | 2 | 1 | 3 | 2 |
| 5.040 | 5 | 5 | 2 | 2 | 2 | 5 | 5 | 5 | 1 | 1 | 1 | 3 |
| 5.041 | 5 | 5 | 1 | 2 | 1 | 5 | 5 | 5 | 1 | 1 | 1 | 2 |
| 5.042 | 5 | 5 | 5 | 2 | 3 | 5 | 5 | 5 | 2 | 2 | 3 | 5 |
| 6.001 | 5 | 5 | 3 | 3 | 5 | 5 | 5 | 4 | 1 | 1 | 3 | 4 |
| 6.002 | 5 | 5 | 2 | 1 | 4 | 5 | 4 | 5 | 1 | 1 | 1 | 2 |
| 6.003 | 5 | 5 | 3 | 1 | 4 | 5 | 5 | 5 | 1 | 1 | 3 | 3 |
| 7.001 | 4 | 3 | 1 | 1 | 2 | 2 | 1 | 2 | 1 | 1 | 1 | 1 |
| 7.002 | 5 | 3 | 1 | 1 | 2 | 2 | 3 | 2 | 1 | 1 | 1 | 2 |
| 8.001 | 5 | 5 | 1 | 1 | 4 | 3 | 2 | 5 | 1 | 1 | 1 | 1 |

*Applied at 500 g/ha
**Applied at 250 g/ha

The invention claimed is:

1. A compound of Formula (I):

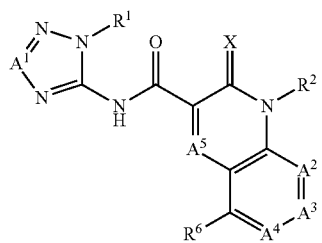

or an agronomically acceptable salt thereof, wherein:
X is O or S;
$A^1$ is CH or N;
$A^2$ is N or $CR^3$;
$A^3$ is N or $CR^4$;
$A^4$ is N or $CR^5$;
$A^5$ is N or CH;
wherein:
$R^1$ is selected from the group consisting of $C_1$-$C_6$ alkyl, $C_1$-$C_6$ haloalkyl and $C_1$-$C_6$alkoxy-$C_1$-$C_3$alkyl;
$R^2$ is selected from the group consisting of hydrogen, $C_1$-$C_6$alkyl, $C_1$-$C_6$haloalkyl, $C_1$-$C_3$alkoxy-$C_1$-$C_3$alkyl, $C_1$-$C_3$haloalkoxy-$C_1$-$C_3$alkyl, $C_1$-$C_3$ alkoxy-$C_1$-$C_3$alkoxy-$C_1$-$C_3$-alkyl, $C_1$-$C_3$alkoxy-$C_1$-$C_3$-haloalkyl, $C_1$-$C_3$-alkoxy-$C_1$-$C_3$-alkoxy-$C_1$-$C_3$-haloalkyl, $C_4$-$C_6$-oxasubstituted cycloalkoxy-$C_1$-$C_3$-alkyl, $C_4$-$C_6$-oxasubstituted cycloalkyl-$C_1$-$C_3$-alkoxy-$C_1$-$C_3$-alkyl, $C_4$-$C_6$-oxasubstituted cycloalkoxy-$C_1$-$C_3$-haloalkyl, $C_4$-$C_6$-oxasubstituted cycloalkyl-$C_1$-$C_3$-alkoxy-$C_1$-$C_3$-haloalkyl, ($C_1$-$C_3$ alkanesulfonyl-$C_1$-$C_3$ alkylamino)-$C_1$-$C_3$alkyl, ($C_1$-$C_3$ alkanesulfonyl-$C_3$-$C_4$cycloalkylamino)-$C_1$-$C_3$alkyl, $C_1$-$C_6$alkylcarbonyl-$C_1$-$C_3$alkyl, $C_3$-$C_6$cycloalkyl-$C_2$-$C_6$alkenyl, $C_2$-$C_6$alkynyl, $C_2$-$C_6$-alkenyl, $C_2$-$C_6$-haloalkenyl, cyano-$C_1$-$C_6$-alkyl, arylcarbonyl-$C_1$-$C_3$-alkyl (wherein the aryl may be optionally substituted with one or more substituents selected from the group consisting of halogen, $C_1$-$C_3$-alkoxy, $C_1$-$C_3$-alkyl, $C_1$-$C_3$ haloalkyl), aryl-$C_1$-$C_6$alkyl, aryloxy-$C_1$-$C_6$alkyl (wherein both cases the aryl may be optionally substituted with one or more substituents selected from the group consisting of halogen, $C_1$-$C_3$-alkoxy, $C_1$-$C_3$-alkyl, $C_1$-$C_3$ haloalkyl), and a three- to ten-membered mono- or bicyclic ring system, which may be aromatic, saturated or partially saturated and can contain from 1 to 4 heteroatoms each independently selected from the group consisting of nitrogen, oxygen and sulphur the ring system being optionally substituted by one or more substituents selected from the group consisting of $C_1$-$C_3$alkyl, $C_1$-$C_3$haloalkyl, $C_2$-$C_3$alkenyl, $C_2$-$C_3$ alkynyl, $C_1$-$C_3$ alkoxy, $C_1$-$C_3$ haloalkoxy, $C_1$-$C_6$alkyl-S(O)$_p$—, $C_1$-$C_6$haloalkyl-S(O)$_p$—, aryl, aryl-S(O)$_p$, heteroaryl-S(O)$_p$, aryloxy, heteroaryloxy, $C_1$-$C_3$ alkoxycarbonyl, $C_1$-$C_3$ alkylamino-S(O)$_p$—, $C_1$-$C_3$ alkylamino-S(O)$_p$—$C_1$-$C_3$ alkyl, $C_1$-$C_3$ dialkylamino-S(O)$_p$—, $C_1$-$C_3$ dialkylamino-S(O)$_p$—$C_1$-$C_3$ alkyl, $C_1$-$C_3$ alkylaminocarbonyl-, $C_1$-$C_3$ alkylaminocarbonyl -$C_1$-$C_3$ alkyl, $C_1$-$C_3$ dialkylaminocarbonyl, $C_1$-$C_3$ dialkylaminocarbonyl-$C_1$-$C_3$ alkyl, $C_1$-$C_3$ alkylcarbonylamino, $C_1$-$C_3$ alkyl-S(O)$_p$-amino, halogen, cyano and nitro; the heteroaryl substituents containing one to three heteroatoms each independently selected from the group consisting of oxygen, nitrogen and sulphur, and wherein the aryl or heteroaryl component may be optionally substituted by one or more substituents selected from the group consisting of halogen, $C_1$-$C_3$alkyl, $C_1$-$C_3$haloalkyl, $C_1$-$C_3$ alkoxy, $C_1$-$C_3$ haloalkoxy, phenyl, cyano and nitro;

$R^3$ is selected from the group consisting of hydrogen, halogen, $C_1$-$C_6$alkyl, $C_1$-$C_6$haloalkyl, $C_1$-$C_6$alkylcarbonyl-$C_1$-$C_3$alkyl, $C_3$-$C_6$cycloalkyl-$C_2$-$C_6$alkenyl-, $C_3$-$C_6$alkynyl, $C_2$-$C_6$-alkenyl, $C_1$-$C_6$alkoxy $C_1$-$C_6$alkyl, cyano-$C_1$-$C_6$-alkyl, arylcarbonyl-$C_1$-$C_3$-alkyl (wherein the aryl may be optionally substituted with one or more substituents selected from the group consisting of halogen, $C_1$-$C_3$-alkoxy, $C_1$-$C_3$-alkyl, $C_1$-$C_3$ haloalkyl), aryl-$C_1$-$C_6$alkyl (wherein the aryl may be optionally substituted with one or more substituents selected from the group consisting of halogen, $C_1$-$C_3$-alkoxy, $C_1$-$C_3$-alkyl, $C_1$-$C_3$ haloalkyl), $C_1$-$C_6$alkoxy$C_1$-$C_6$alkoxy $C_1$-$C_6$alkyl, aryl, a 5 or 6-membered heteroaryl, a 5 or 6-membered heteroaryl-$C_1$-$C_3$-alkyl and heterocyclyl-$C_1$-$C_3$-alkyl, the heteroaryl or heterocyclyl containing one to three heteroatoms each independently selected from the group consisting of oxygen, nitrogen and sulphur, and wherein the aryl, heterocyclyl or heteroaryl component may be optionally substituted by one or more substituents selected from the group consisting of halogen, $C_1$-$C_3$alkyl, $C_1$-$C_3$haloalkyl and $C_1$-$C_3$ alkoxy, cyano and nitro;

$R^4$ is selected from the group consisting of hydrogen, cyano, nitro, halogen, hydroxy, sulfhydryl, $C_1$-$C_6$alkyl, $C_3$-$C_6$cycloalkyl, $C_1$-$C_6$haloalkyl, $C_2$-$C_6$haloalkenyl, $C_2$-$C_6$alkenyl, aryl-$C_2$-$C_6$alkenyl, $C_2$-$C_6$alkynyl, $C_1$-$C_6$alkoxy, $C_4$-$C_7$ cycloalkoxy, $C_1$-$C_6$haloalkoxy, $C_1$-$C_6$alkyl-S(O)$_p$, $C_3$-$C_6$-cycloalkyl -S(O)$_p$, $C_1$-$C_6$-haloalkyl-S(O)$_p$, $C_3$-$C_6$halocycloalkyl-S(O)$_p$, $C_1$-$C_6$alkylcarbonylamino, ($C_1$-$C_6$alkylcarbonyl)$C_1$-$C_3$ alkylamino, ($C_3$-$C_6$cycloalkylcarbonyl)amino, ($C_3$-$C_6$cycloalkylcarbonyl)$C_1$-$C_3$alkylamino, arylcarbonylamino, (arylcarbonyl)-$C_{1-3}$alkylamino, (heteroarylcarbonyl)amino, (heteroarylcarbonyl)$C_1$-$C_3$alkylamino, amino, $C_1$-$C_6$alkylamino, $C_2$-$C_6$dialkylamino, $C_2$-$C_6$alkenylamino, $C_1$-$C_6$alkoxy-$C_2$-$C_6$-alkylamino, ($C_1$-$C_6$alkoxy-$C_2$-$C_4$-alkyl)-$C_1$-$C_6$-alkylamino, $C_3$-$C_6$ cycloalkylamino, $C_3$-$C_6$ cyclohaloalkylamino, $C_1$-$C_3$alkoxy-$C_3$-$C_6$ cycloalkylamino, $C_3$-$C_6$ alkynylamino, dialkylamino in which the substituents join to form a 4-6 membered ring optionally containing oxygen optionally substituted by $C_1$-$C_3$-alkoxy and/or halogen, $C_2$-$C_6$dialkylaminosulfonyl, $C_1$-$C_6$alkylaminosulfonyl, $C_1$-$C_6$alkoxy-$C_1$-$C_6$alkyl, $C_1$-$C_6$alkoxy-$C_2$-$C_6$alkoxy, $C_1$-$C_6$alkoxy-$C_2$-$C_6$ alkoxy -$C_1$-$C_6$-alkyl, $C_3$-$C_6$alkenyl-$C_2$-$C_6$alkoxy, $C_3$-$C_6$alkynyl-$C_1$-$C_6$alkoxy, $C_1$-$C_6$alkoxycarbonyl, $C_1$-$C_6$alkylcarbonyl, $C_1$-$C_4$alkylenyl-S(O)$_p$-$R^7$, $C_1$-$C_4$alkylenyl-(CO)$_2$-$R^7$, $C_1$-$C_4$alkylenyl-(CO)N-$R^7R^7$, aryl, aryl $C_1$-$C_3$alkyl, aryl-S(O)$_p$, heteroaryl-S(O)$_p$, aryloxy, a 5-membered heteroaryl, a 6-membered heteroaryl, heteroaryl $C_1$-$C_3$ alkyl and heteroaryloxy, the heteroaryl containing one to three heteroatoms, each independently selected from the group consisting of oxygen, nitrogen and sulphur, wherein the aryl or heteroaryl component may be optionally substituted by one or more substituents selected from the group consisting of $C_1$-$C_3$alkyl, $C_1$-$C_3$haloalkyl, $C_1$-$C_3$ alkoxy, $C_1$-$C_3$haloalkoxy, halo, cyano and nitro;

$R^5$ is selected from the group consisting of hydrogen, fluoro, chloro, hydroxy, $C_1$-$C_3$ haloalkyl and methyl;

$R^6$ is selected from the group consisting of hydrogen, chloro, fluoro and methyl;

$R^7$ is independently selected from the group consisting of hydrogen and $C_1$-$C_6$alkyl; and p is 0, 1 or 2.

2. The compound according to claim 1, selected from the group consisting of (i) wherein $A^2$ is $CR^3$, $A^3$ is $CR^4$, $A^4$ is $CR^5$ and $A^5$ is CH, (ii) wherein $A^2$ is $CR^3$, $A^3$ is N, $A^4$ is $CR^5$ and $A^5$ is CH, (iii) wherein $A^2$ is N, $A^3$ is $CR^4$, $A^4$ is $CR^5$ and $A^5$ is CH, (iv) wherein $A^2$ is $CR^3$, $A^3$ is $CR^4$, $A^4$ is N and $A^5$ is CH, (v) wherein $A^2$ is $CR^3$, $A^3$ is $CR^4$, $A^4$ is $CR^5$ and $A^5$ is N and (vi) wherein $A^2$ is N, $A^3$ is $CR^4$, $A^4$ is $CR^5$ and $A^5$ is N.

3. A The compound according to claim 2, wherein (i) $A^2$ is $CR^3$, $A^3$ is $CR^4$, $A^4$ is $CR^5$ and $A^5$ is N or (ii) wherein $A^2$ is N, $A^3$ is $CR^4$, $A^4$ is $CR^5$ and $A^5$ is CH.

4. The compound according to claim 1, wherein $R^2$ is selected from the group consisting of $C_1$-$C_6$alkyl, aryl, a 5-membered heteroaryl and a 6-membered heteroaryl containing one to three heteroatoms each independently selected from the group consisting of oxygen, nitrogen and sulphur, and wherein the aryl or heteroaryl may be optionally substituted by one or more substituents selected from the group consisting of halogen, $C_1$-$C_3$alkyl, $C_1$-$C_3$haloalkyl, $C_1$-$C_3$ alkoxy, $C_1$-$C_3$ haloalkoxy, $C_1$-$C_6$alkyl-S(O)$_p$—, $C_1$-$C_6$haloalkyl-S(O)$_p$—, cyano and nitro.

5. The compound according to claim 4, wherein $R^2$ is phenyl optionally substituted by one or more substituents selected from the group consisting of halogen, $C_1$-$C_3$alkyl, $C_1$-$C_3$haloalkyl, $C_1$-$C_3$ alkoxy, $C_1$-$C_3$ haloalkoxy, methylthio-, cyano and nitro.

6. The compound according to claim 1, wherein $A^1$ is N and $R^1$ is methyl or ethyl.

7. The compound according to claim 1, wherein $R^3$ is selected from the group consisting of hydrogen, halogen and $C_1$-$C_6$alkyl.

8. The compound according to claim 1, wherein $R^4$ is selected from the group consisting of hydrogen, halogen, $C_1$-$C_6$alkyl and $C_1$-$C_6$haloalkyl.

9. The compound according to claim 1, wherein $R^5$ is hydrogen, chloro or fluoro.

10. The compound according to claim 1, wherein $R^6$ is selected from the group consisting of hydrogen, chloro, fluoro and methyl.

11. A herbicidal composition comprising a compound according to claim 1 and an agronomically acceptable formulation adjuvant.

12. The herbicidal composition according to claim 11, further comprising at least one additional pesticide.

13. The herbicidal composition according to claim 12, wherein the additional pesticide is a herbicide or herbicide safener.

14. A method of controlling weeds at a locus comprising the step of applying to said locus a weed controlling amount of a composition according to claim 11.

* * * * *